United States Patent [19]

Chi et al.

[11] Patent Number: 5,527,832
[45] Date of Patent: Jun. 18, 1996

[54] ANTIINFLAMMATORY AND ANALGESIC TRANSDERMAL GEL

[75] Inventors: Sang-Cheol Chi, Kyunggi-do; Hyun-Kwang Tan, Seoul, both of Rep. of Korea; Heung-Won Chun, Athens, Ga.

[73] Assignee: Il-Dong Pharm. Co., Ltd., Seoul, Rep. of Korea

[21] Appl. No.: 207,598

[22] Filed: Mar. 9, 1994

[51] Int. Cl.$^6$ .................................................. A61K 47/32
[52] U.S. Cl. ...................... 514/772.4; 514/944; 424/443
[58] Field of Search ................................ 514/772.4, 944; 424/443

[56] References Cited

U.S. PATENT DOCUMENTS

| | | | |
|---|---|---|---|
| 4,393,076 | 7/1983 | Noda et al. | 424/317 |
| 4,534,980 | 8/1985 | Itoh et al. | 514/570 |
| 4,849,418 | 7/1989 | Lohner | 514/163 |
| 4,956,184 | 9/1990 | Kross | 424/661 |
| 5,256,396 | 10/1993 | Piechota, Jr. | 424/49 |

FOREIGN PATENT DOCUMENTS

| | | |
|---|---|---|
| 56-138882 | 3/1983 | Japan . |
| 56-138881 | 3/1983 | Japan . |
| 58-83622 | 5/1983 | Japan . |
| 61-238723 | 10/1986 | Japan . |

OTHER PUBLICATIONS

Yano et al., "Skin Permeability of Various . . .", Life Sciences, vol. 39, pp. 1043–1050, 1986.

*Primary Examiner*—D. Gabrielle Phelan
*Attorney, Agent, or Firm*—Birch, Stewart, Kolasch & Birch

[57] ABSTRACT

Transdermal gels comprising (1) ketoprofen as an effective component, (2) poloxamer, (3) one or more agents selected from ethyl alcohol, isopropyl alcohol, propylene glycol, polyethylene glycol and glycerin, (4) one or more agents selected from the group consisting of lauric acid, oleic acid, capric acid, myristic acid, lauryl alcohol, oleyl alcohol and menthol, (5) water or a buffer solution. The gels form thin and pliable films, which are easily washable with water. They possess prolonged antiinflammatory and analgesic activities and physicochemical stability with less systemic side effects and gastric irritation.

2 Claims, No Drawings

ANTIINFLAMMATORY AND ANALGESIC TRANSDERMAL GEL

BACKGROUND OF THE INVENTION

1. Technical Background

The present invention relates to an antiinflammatory and analgesic transdermal gel containing a nonsteroidal antiinflammatory drug which is a propionic acid derivative as an effective ingredient. In particular, the present invention relates to a novel antiinflammatory and analgesic transdermal gel which is water-soluble and provides comparable antiinflammatory and analgesic activities to oral administered compositions while significantly reducing the systemic side effects and the gastrointestinal irritation associated with the oral administration of propionic acid derivatives.

2. The Prior Art

Typical examples of the nonsteroidal anti inflammatory propionic acid derivatives include ketoprofen, ibuprofen, flurbiprofen, naproxen, fenoprofen, benoxaprofen, indoprofen, pirprofen, carprofen, oxaprozin, pranoprofen, suprofen, alminoprofen, butibufen and fenbufen, etc. They have potent antiinflammatory and analgesic activities and are widely used for the treatment of rheumatic arthritis and its related conditions. Conventionally, these drugs have been administered orally in the form of solid preparations such as tablets and capsules. However, they have accompanied systemic side effects or gastrointestinal irritation following their oral administration. In order to reduce these side effects, these drugs have been formulated as transdermal preparations based on the fact that the skin permeability of these nonsteroidal antiinflammatory drugs are known to be relatively higher than other nonsteroidal antiinflammatory drugs. For examples, JP 58-39616, JP 58-83622, JP 58-103311, JP 61-238723 and U.S. Pat. Nos. 4,393,076 and 4,534,980 disclosed formulating nonsteroidal antiinflammatory drugs of propionic acid derivatives into transdermal preparations, generally an ointment or a cream. They claimed that the systemic side effects and gastrointestinal irritation of these drugs were significantly reduced while satisfied therapeutic effects were obtained. In these patents, they usually used carboxyvinyl polymer or hydroxypropylmethylcellulose as a gel base in the formulation of transdermal preparations of the drugs. However, the skin permeations of the drugs from their preparations were not enough to achieve pharmacological effects comparable to the oral administration of the drugs due to the low percutaneous absorption of the drugs from the preparations and, thus, a large amount of the preparation needed to be applied to achieve a desired efficacy.

As a result of extensive investigations with attempts to improve the shorcomings of the existing patents and products, the present inventors have succeeded in establishing a novel transdermal gel containing a nonsteroidal antiinflammatory drug which is a propionic acid derivative. The gel is water-soluble, has high skin permeation rate and, thus, excellent antiinflammatory and analgesic activities comparable to its oral administration. It, also, showed lowered systemic side effects and gastrointestinal irritation and good physicochemlcal stability.

SUMMARY OF THE INVENTION

The present invention provides an antiinflammatory and analgesic transdermal gel which comprises, by weight, 0.5%–5% of a nonsteroidal antiinflammatory drug of a propionic acid derivative as an effective ingredient; 10–30% of poloxamer as a gel forming agent; 3–30% of one or more agents selected from a lower alcohol, propylene glycol, polyethylene glycol and glycerin; 0.3–10% of one or more agents selected from fatty acids, fatty alcohols and menthol; and total to 100% with water or a buffer solution.

DETAILED DESCRIPTION OF THE INVENTION

The transdermal gels of the present invention can be prepared by dissolving a mixture comprising a nonsteroidal antiinflammatory drug of a propionic acid derivative such as ketoprofen, flurbiprofen, ibuprofen, naproxen, fenoprofen, benoxaprofen, indoprofen, pirprofen, carprofen, oxaproztn, pranoprofen, suprofen, alminoprofen, butibufen and fenbufen, etc; poloxamer; and one or more agents selected from lower alcohol, glycerin, propylene glycol and polyethylene glycol; one or more agent enhancers selected from fatty acids, fatty alcohols and menthol; and, if necessary, one or more other agent including a preservative, a flavor, in water or a buffer solution.

More specifically, the lower alcohol used in the present invention may be ethanol and isopropyl alcohol, and poloxamer derivatives may be poloxamer 407 and poloxamer 338, poloxamer 237 and others. The concentrated aqueous solution of poloxamer, used as a gel forming agent of this invention, is a low viscous transparent liquid at refrigerator temperature or lower, but turns to a clear semisolid gel on heating to room or body temperature. The polymer also possesses several properties which make it particularly suitable for use in the formulation of transdermal dosage forms. These include low toxicity and skin irritation, excellent compatibility with other chemicals, high solubilizing capacity for different drugs and good drug release characteristics.

Polyethylene glycol may be polyethylene glycol 200, polyethylene glycol 300, polyethylene glycol 400, polyethylene glycol 600, polyethylene glycol 1000 and others. Fatty acids may be lauric acid, oleic acid, captic acid, myristic acid and others, and fatty alcohols may be lauryl alcohol, oleyl alcohol and others.

In the present invention, the pH of the gel may be 4–8 which is usual for the conventional gel forming agent, but it is desirable to use a buffer solution having a pH value around the pKa value of each active compound.

The preservative may be benzoic acid, sodium benzoate, methyl p-hydroxybenzoate, ethyl p-hydroxybenzoate, propyl p-hydroxybenzoate, butyl p-hydroxybenzoate or a mixture thereof. The gel compositions of this invention comprise desirably 0.5–5% of nonsteroidal antiinflammatory drug of propionic acid derivative; 10–30% of poloxamer; and 3–30% of lower alcohol or polyethylene glycol or propylene glycol or glycerin; 0.3–10% fatty acid or fatty alcohol or menthol.

When the gel of the present invention is applied on skin, it forms a thin and pliable film from which the drug is released slowly and continuously, resulting in prolonged antiinflammatory and analgesic activities which last for one day. Propylene glycol, polyethylene glycol and glycerin act as a moisturizer as well as cosolvent. Fatty acid or fatty alcohol or menthol act as a penetration enhancer.

The present transdermal gels can be prepared simply as follows: the drug and poloxamer are heated at a temperature higher than 90° C. to obtain a homogeneous liquid mixture, and then the mixture is cooled to 40°–60° C. Separately, water or a buffer solution in which the other additives have been dissolved is prepared and added into the above liquified mixture. When it is cooled to room temperature or in the refrigerator, the gel forms. The produced transdermal gels of nonsteroidal antiinflammatory drug of propionic acid derivatives are water-soluble, transparent with good texture, and exhibit excellent antiinflammatory and analgesic activity with less gastrointestinal irritation, as shown in the following Experiments.

Hereafter, the present invention will be described in more detail with reference to the following examples, but is not deemed to be limited only thereto. Throughout the examples, all percents are by weight.

EXAMPLE 1

| | |
|---|---|
| Ketoprofen | 3% |
| Poloxamer 407 | 15% |
| Polyethylene glycol 300 | 3% |
| Ethanol | 18.5% |
| Menthol | 0.3% |
| Methyl p-hydroxybenzoate | 0.17% |
| Propyl p-hydroxybenzoate | 0.02% |
| pH 4.5 buffer solution | 60.01% |

Three grams of ketoprofen and 15 g of potoxamer 407 were heated at 105° C. for 10 minutes to obtain a liquified mixture and then cooled to 60° C. Separately, 0. 17 g of methyl p-hydroxybenzoate, 0.02 g of propyl p-hydroxybenzoate and 0.3 g of menthol were dissolved in 18.5 g of ethanol, and 3 g of polyethylene glycol 300 was mixed with 60.01 g of pH 4.5 buffer solution. After the alcohol solution was mixed with the above mixture at 60° C., the aqueous solution was added into the final mixture at 60° C. to obtain a ketoprofen gel.

EXAMPLE 2

| | |
|---|---|
| Ketoprofen | 3% |
| Poloxamer 407 | 17% |
| Polyethylene glycol 4000 | 5% |
| Ethanol | 20% |
| Lauric acid | 5% |
| Water | 50% |

Three grams of ketoprofen and 17 g of poloxamer 407 were heated at 105° C. for 10 minutes to obtain a liquified mixture and then cooled to 60° C. Separately, 5 g of lauric acid was dissolved in the mixture of 5 g of polyethyleneglycol 4000 and 20 g of ethanol, which was mixed into the above liquified mixture at 60° C. Finally, 50 g of water was added under vigorous stirring to obtain a ketoprofen gel.

EXAMPLE 3

| | |
|---|---|
| Ketoprofen | 1% |
| Poloxamer 407 | 20% |
| pH 4.5 buffer solution | 79% |

One gram of ketoprofen and 20 g of poloxamer 407 were heated at 105° C. for 10 minutes to obtain a liquified mixture. After cooled to room temperature, 79 g of pH 4.5 buffer solution was added into the liquified mixture under stirring and kept standing in a refrigerator overnight to obtain a ketoprofen gel.

EXAMPLE 4

| | |
|---|---|
| Ibuprofen | 1% |
| Poloxamer 407 | 20% |
| Propylene glycol | 10% |
| Ethanol | 20% |
| NaCl | 0.2% |
| Water | 48.8% |

One gram of ibuprofen and 20 g of poloxamer 407 were heated at 110° C. for 15 minutes to obtain a liquified mixture and cooled to 60° C. Separately, a mixture of 10 g of propylene glycol, 20 g of ethanol 48.8 g of water and 0.2 g of sodium chloride was prepared and added into the above liquified mixture at 60° C. to obtain an ibuprofen gel.

EXAMPLE 5

| | |
|---|---|
| Ibuprofen | 3% |
| Poloxamer 407 | 15% |
| Polyethylene glycol 300 | 10% |
| Ethanol | 20% |
| Lauryl alcolhol | 5% |
| Water | 47% |

Three grams of ibuprofen and 15 g of poloxamer 407 were heated at 110° C. for 15 minutes to obtain a liquified mixture and then cooled to 60° C. Separately, 5 g of lauryl alcohol was dissolved in the mixture of 10 g of polyethyleneglycol 300 and 20 g of ethanol, which was added into the above liquified mixture at 60° C. Finally, 47 g of water was added under vigorous stirring to obtain an ibuprofen gel.

EXAMPLE 6

| | |
|---|---|
| Ibuprofen | 3% |
| Poloxamer 237 | 30% |
| Polyethylene glycol 300 | 5% |
| Ethanol | 10% |
| pH 4 buffer solution | 52% |

Three grams of flurbiprofen and 30 g of poloxamer 237 were heated at 110° C. for 10 minutes to obtain a liquified mixture and cooled to 60° C. Into this mixture, 5 g of polyethylene glycol 300, 10 g of ethanol and 52 g of pH 4 buffer solution were added at 60° C. to obtain an ibuprofen gel.

EXAMPLE 7

| | |
|---|---|
| Flurbiprofen | 3% |
| Poloxamer 407 | 17.5% |
| Propylene glycol | 10% |
| Ethanol | 20% |
| Lauric acid | 5% |
| pH 4 buffer solution | 44.5% |

Three grams of flurbiprofen and 17.5 g of poloxamer 407 were heated at 115° C. for 10 minutes to obtain a liquified mixture and then cooled to 60° C. Separately, 5 g of lauric acid was dissolved in the mixture of log of propylene glycol and 20 g of ethanol, which was added into the above liquified mixture at 60° C. Finally, 44.5 g of pH 4 buffer solution was added under vigorous stirring to obtain a flurbiprofen gel.

EXAMPLE 8

| Naproxen | 5% |
|---|---|
| Poloxamer 407 | 20% |
| Polyethylene glycol 300 | 5% |
| Ethanol | 20% |
| pH 4 buffer solution | 50% |

Five grams of naproxen and 20 g of poloxamer 407 were heated at 160° C. for 10 minutes to obtain a liquified mixture and cooled to 60° C. Separately, 20 g of ethanol and 5 g of polyethylene glycol 300 was mixed in 50 g of pH 4.0 buffer solution, and added into the above liquified mixture at 60° C. to obtain a naproxen gel.

EXAMPLE 9

| Oxaprozin | 1% |
|---|---|
| Poloxamer 407 | 20% |
| Propylene glycol | 10% |
| Ethanol | 10% |
| Menthol | 0.5% |
| Water | 58.5% |

One gram of oxaprozin and 20 g of poloxamer 407 were heated at 160° C. for 10 minutes to obtain a liquified mixture and cooled to 60° C. Separately, 0.5 g of menthol was dissolved in log ethanol and mixed with the mixture. Finally a solution of 58.5 g of water and log of propylene glycol was added into the mixture at 60° C. to obtain an oxaprozin gel.

EXAMPLE 10

| Pirprofen | 2% |
|---|---|
| Poloxamer 407 | 20% |
| Glycerin | 5% |
| Isopropyl alcohol | 20% |
| Water | 53% |

Two grams of pirprofen and 20 g of poloxamer 407 were heated at 105° C. for 10 minutes to obtain a liquified mixture and cooled to 60° C. Separately, 20 g of isopropyl alcohol and 5 g of glycerin was mixed in 53 g of water, and added into the above liquified mixture to obtain a pirprofen gel.

EXAMPLE 11

| Alminoprofen | 1% |
|---|---|
| Poloxamer 407 | 25% |
| Propylene glycol | 15% |
| Ethanol | 5% |
| Water | 54% |

One gram of alminoprofen and 25 g of poloxamer 407 were heated at 110° C. for 10 minutes to obtain a liquified mixture and cooled to 60° C. Separately, 5 g of ethanol and 15 g of propylene glycol was mixed in 54 g of water, and added into the above liquified mixture at 60° C. to obtain an alminoprofen gel.

EXAMPLE 12

| Butibufen | 1% |
|---|---|
| Poloxamer 407 | 20% |
| Polyethylene glycol 200 | 5% |
| Isopropyl alcohol | 15% |
| Water | 59% |

One gram of butibufen and 20 g of poloxamer 407 were heated at 90° C. for 10 minutes to obtain a liquified mixture and cooled to 40° C. Separately, 15 g of isopropyl alcohol and 5g of polyethylene glycol 200 was mixed in 59 g of water, and added into the above liquified mixture at 40° C. to obtain a butibufen gel.

The antiinflammatory and analgesic transdermal gels of the present invention prepared as above exhibited excellent pharmacological activities with less gastric irritation and showed good physicochemical stability as shown in the Experiments below.

Experiment 1

Antiinflammatory activity on carrageenan-induced paw edema in rats:

Male Sprague-Dawley rats weighing about 200 g were used as the test animals. Three hours before carrageenan injection, each gel in the Example 1, 4 and 7 was applied on the left hind paw of the rats at the dose of 50 mg. Then, 0.1 ml of 1% carrageenan in physiological saline was injected into the paw subplantarly. Immediately and three hours after the carrageenan injection, the volume of the paw was measured using a plethysmometer(Ugo Basile Co. Italy), and the percent swelling of the paw and the percent inhibition of the edema formation were calculated as follows:

$$\% \text{ swelling} = \frac{\text{paw volume at 3 hrs after carrageenan injection} - \text{initial paw volume}}{\text{initial paw volume}} \times 100$$

$$\% \text{ inhibition} = \left[ 1 - \frac{\% \text{ swelling of drug-treated group}}{\% \text{ swelling of control group}} \right] \times 100$$

The results are presented in Table 1.

TABLE 1

| Group | No. of Rat | % Swelling* | % Inhibition |
|---|---|---|---|
| Control | 8 | 77.2 ± 19.8 | — |
| Example 1 (ketoprofen gel) | 6 | 25.6 ± 6.2** | 66.8 |
| Example 4 (ibuprofen gel) | 6 | 32.2 ± 9.6** | 58.3 |
| Example 7 (flurbiprofen gel) | 6 | 30.1 ± 8.8** | 61.0 |

*Mean value ± S.D.
**Significantly different as compared to the control ($P < 0.05$)

As can be seen in Table 1, the above transdermal gels according to the present invention exhibited significant decrease of % swelling of the paw compared to the control. The % inhibition of the edema formation by the gels was in the range of 58 to 66%, which is the maximum inhibition, 60%, obtainable with this model.

Experiment 2

Antiinflammatory activity on adjuvant-induced arthritis inhibition in rats:

Male Sprague-Dawley rats weighing about 250 g were anesthetized slightly and an emulsion (6 mg/ml) of Mycobacterium butyricum in mineral oil was inoculated subplantarly into the left hind paw of rats. Each gel in the Example 1, 4 and 7 were applied on the inoculated paw at the dose of 50 mg once daily from 12th day to 20th day after the injection. On the 21th day after the injection, the volume of the paw was measured according to the method in the Experiment 1 to determine the edema formation of the paw injected with the adjuvant. The results are presented in Table 2 below.

TABLE 2

| Group | No. of Rat | % Swelling* |
|---|---|---|
| Control | 10 | 2.30 ± 0.37 |
| Example 1 (ketoprofen gel) | 10 | 0.79 ± 0.28** |
| Example 4 (ibuprofen gel) | 10 | 0.95 ± 0.31** |
| Example 7 (flurbiprofen gel) | 10 | 1.14 ± 0.35** |

*Mean value ± S.D.
**Significantly different as compared to the control (P < 0.05)

As shown in Table 2, the transdermal gels according to the present invention have excellent ant±inflammatory activity since they decreased paw edema induced by the subplantar injection of adjuvant, by more than 50% compared with the control group.

Experiment 3

Percutaneous absorption:

Four male Sprague-Dawley rats weighing 200 g ±20 g were used to evaluate the percutaneous absorption of ketoprofen from the gel of Example 1. Prior to application of the gel, hair at the rat ventral skin area was carefully removed with an electrical clipper. Fifty mg of the gel was uniformly applied over the area of approximately 2 cm ×3 cm with gentle rubbing. At predetermined time intervals, 250 ul of blood was collected into a microcentrifuge tube containing heparin to obtain a plasma sample. The concentration of ketoprofen in rat plasma was quantitated with High Performance Liquid Chromatography. The results are presented in Table 3 below.

TABLE 3

| Time Elapsed (hr) | Concentration of Ketoprofen in Plasma | Time Elapsed (hr) | Concentration of Ketoprofen in Plasma |
|---|---|---|---|
| 1 | 225.9 ± 63.1 | 10 | 404.5 ± 89.1 |
| 2 | 452.8 ± 68.1 | 12 | 341.5 ± 59.0 |
| 3 | 739.1 ± 216.9 | 16 | 263.3 ± 21.6 |
| 4 | 798.8 ± 178.8 | 24 | 183.9 ± 33.3 |
| 6 | 810.0 ± 174.9 | 36 | 76.6 ± 11.4 |
| 8 | 588.7 ± 120.1 | 48 | 63.5 ± 6.1 |

*Mean value ± S.D.

The maximum concentration of ketoprofen after its oral administration to rats are known to appear at 0.25–0.5 hrs postdose. After the transdermal application of the gel of Example 1, however, the absorption of ketoprofen was so slowered that the maximum concentration of the drug was 6 hrs postdose as can be seen in Table 3. And, also, the ketoprofen concentration in plasma was maintained plateau relatively over several hours after the transdermal application, even though much lower than that after the oral administration of the drug.

Experiment 4

Gastric ulcer formation:

Male Sprague-Dawley rats weighing around 200 g were used as the test animals. Food was withheld from the rats for 24 hrs prior to dosing while water was allowed freely throughout the experiment. Each gel in the Example 1, 4 and 7 was applied gently, at the dose of 50 mg/kg, on the dorsal skin of 2 cm ×3 cm where the hair was removed. As a reference, the rats of the control group were administrated ketoprofen orally as a suspension in physiological saline at the dose of 10 mg/kg. Six hours after the administration, the rats were sacrificed and ulcer formation in the stomach was scored as follows: 0; normal, 1; reddened mucosa, 2; one to four small ulcer (smaller than 2 mm in diameter). 3; more than four small ulcer or one large ulcer (larger than 2 mm in diameter), 4; more than one large ulcer. The score of two or higher was regarded as ulcer formation. The results are presented in Table 4 below.

TABLE 4

| Administration Route | Drug or Preparation | Dose* | No. of Rat Ulcer Is Produced | Average Ulcer Score |
|---|---|---|---|---|
| Oral | Control (ketoprofen) | 10 mg/kg | 6/6 | 2.91 |
| | Control (ibuprofen) | 10 mg/kg | 6/6 | 2.53 |
| | Control (flurbiprofen) | 10 mg/kg | 5/6 | 2.46 |
| Transdermal | Example 1 (ketoprofen gel) | 50 mg/kg | 2/6 | 1.88 |
| | Example 4 (ibuprofen gel) | 50 mg/kg | 1/6 | 1.19 |
| | Example 7 (flurbiprofen gel) | 50 mg/kg | 1/6 | 0.95 |

*as ketoprofen

As can be seen in Table 3, when nonsteroidal antiinflammatory drugs of propionic acid derivatives were formulated into gels according to the present invention and administrated transdermally, gastric ulcer formation was much lower even with 5-fold doses than the oral administration. The ulcer formation were also observed after the percutaneous administration of the gels, indicating that a significant amount of the drug permeated the skin and was absorbed into the blood circulation.

Experiment 5

Stability test:

The gels in Example 1, 4 and 7 were stored at 4° C., 25° C. and 40° C. After 6 months, the samples were examined whether the initial texture of each gel was maintained or not. The change of color was tested visually against white background and samll quantities of the gels were subjected to microscopic examination to identify any recrystallization of the drug. The amount of the drug in the gel was quantitated using High Performance Liquid Chromatography and the results are presented in Table 5 below.

TABLE 5

| | Storage Temperature | Amount Remaining(%)* | Appearance | Recrystallization |
|---|---|---|---|---|
| Example 1 (ketoprofen gel) | 4° C. | 103.2 | no change | not observed |
| | 25° C. | 98.2 | no change | not observed |
| | 40° C. | 99.2 | no change | not observed |
| Example 4 (ibuprofen gel) | 4° C. | 102.1 | no change | not observed |
| | 25° C. | 100.6 | no change | not observed |
| | 40° C. | 100.2 | no change | not observed |
| Example 7 (flurbiprofen gel) | 4° C. | 98.8 | no change | not observed |
| | 25° C. | 97.1 | no change | not observed |
| | 40° C. | 99.5 | no change | not observed |

*Percent relative to the initial amount

As shown in Table 4, any change of appearance or recrystallization in the gel was observed and little change of the amount of drug in the gel was detected compared to the initial amount, indicating excellent physicochemical stability of the gel.

What is claimed is:

1. An anti-inflammatory and analgesic transdermal gel which consists essentially of, by weight, 0.5%–5% of ketoprofen as an effective ingredient;

10%–30% of a poloxamer as a gel forming agent;

3–30% of one or more agents selected from the group consisting of ethyl alcohol, isopropyl alcohol, propylene glycol, polyethylene glycol and glycerin;

0.3–10% of one or more agents selected from the group consisting of lauric acid, oleic acid, capric acid, myristic acid, lauryl alcohol, oleyl alcohol and menthol;

optionally, preservatives and flavors; and total to 100% with water or a buffer solution.

2. The transdermal gel according to claim 1, wherein the gel pH is controlled to a value close to the pKa of ketoprofen.

* * * * *